(12) United States Patent
Diaz et al.

(10) Patent No.: US 9,733,805 B2
(45) Date of Patent: Aug. 15, 2017

(54) GENERATING PROCEDURES FOR ENTERING DATA PRIOR TO SEPARATING A LIQUID INTO COMPONENTS

(71) Applicant: Terumo BCT, Inc., Lakewood, CO (US)

(72) Inventors: Luis Diaz, Littleton, CO (US); Allan Gallano, Highlands Ranch, CO (US)

(73) Assignee: TERUMO BCT, INC., Lakewood, CO (US)

( * ) Notice: Subject to any disclaimer, the term of this patent is extended or adjusted under 35 U.S.C. 154(b) by 284 days.

(21) Appl. No.: 13/927,841

(22) Filed: Jun. 26, 2013

(65) Prior Publication Data

US 2013/0346901 A1 Dec. 26, 2013

Related U.S. Application Data

(60) Provisional application No. 61/664,566, filed on Jun. 26, 2012.

(51) Int. Cl.
| | |
|---|---|
| *G06F 3/048* | (2013.01) |
| *G06F 3/0484* | (2013.01) |
| *G06F 3/0481* | (2013.01) |
| *G01N 33/48* | (2006.01) |
| *G06K 7/14* | (2006.01) |
| *G06F 19/00* | (2011.01) |

(52) U.S. Cl.
CPC .......... *G06F 3/0484* (2013.01); *G01N 33/48* (2013.01); *G06F 3/0481* (2013.01); *G06F 19/3406* (2013.01); *G06K 7/1434* (2013.01)

(58) Field of Classification Search
CPC ...... G06F 8/34; G06F 3/04847; G06F 3/0481; G06F 19/3406; G05B 2219/23258; G05B 19/0426; G01N 35/1067; G01N 33/48; B01L 3/56; B01L 3/545; G06K 17/00
USPC .................................................. 715/771, 224
See application file for complete search history.

(56) References Cited

U.S. PATENT DOCUMENTS

| | | | |
|---|---|---|---|
| 3,427,896 A | 2/1969 | Hartman, Jr. | |
| 3,640,388 A | 2/1972 | Ferrari | |
| 3,718,133 A | 2/1973 | Perry et al. | |

(Continued)

FOREIGN PATENT DOCUMENTS

| | | |
|---|---|---|
| DE | 2636290 A1 | 2/1978 |
| DE | 20015684 U1 | 3/2001 |

(Continued)

OTHER PUBLICATIONS

Baxter Healthcare Corporation, "CS-3000 Plus Parameter Changes", undated, Baxter Healthcare Corporation.

(Continued)

*Primary Examiner* — Joy Weber
(74) *Attorney, Agent, or Firm* — Terumo BCT, Inc. IP Law Dept.

(57) ABSTRACT

Described are embodiments that are useful for generating procedures for entering data prior to separating liquid into liquid components. The embodiments are applicable to procedures for entering data prior to separating blood into components. Graphical elements are displayed that allow a user to appreciate the workflow of someone who implements the procedures. As a result, the user can create a procedure that is simple, efficient, and is less prone to errors.

5 Claims, 12 Drawing Sheets

(56) References Cited

U.S. PATENT DOCUMENTS

| | | |
|---|---|---|
| 3,737,096 A | 6/1973 | Jones et al. |
| 3,747,843 A | 7/1973 | Joyce |
| 3,812,724 A | 5/1974 | Curtz et al. |
| 3,921,898 A | 11/1975 | Finkel |
| 3,954,414 A | 5/1976 | Samson, Jr. et al. |
| 3,957,197 A | 5/1976 | Sartory et al. |
| 4,010,894 A | 3/1977 | Kellogg et al. |
| 4,091,989 A | 5/1978 | Schlutz |
| 4,094,461 A | 6/1978 | Kellogg et al. |
| 4,098,456 A | 7/1978 | Bayham |
| 4,114,802 A | 9/1978 | Brown |
| 4,157,781 A | 6/1979 | Maruyama |
| 4,191,469 A | 3/1980 | Flossdorf et al. |
| 4,231,366 A | 11/1980 | Schael |
| 4,295,386 A | 10/1981 | Zhivotov |
| 4,296,882 A | 10/1981 | Kobayashi |
| 4,299,218 A | 11/1981 | Knigge et al. |
| 4,303,193 A | 12/1981 | Latham, Jr. |
| 4,370,983 A | 2/1983 | Lichtenstein |
| 4,379,452 A | 4/1983 | DeVries |
| 4,412,831 A | 11/1983 | Avery et al. |
| 4,425,112 A | 1/1984 | Ito |
| 4,436,620 A | 3/1984 | Bellotti et al. |
| 4,447,191 A | 5/1984 | Bilstad et al. |
| 4,457,750 A | 7/1984 | Hill |
| 4,458,539 A | 7/1984 | Bilstad et al. |
| 4,479,760 A | 10/1984 | Bilstad et al. |
| 4,481,827 A | 11/1984 | Bilstad et al. |
| 4,493,691 A | 1/1985 | Calari |
| 4,526,515 A | 7/1985 | DeVries |
| 4,526,574 A | 7/1985 | Pekkarinen |
| 4,582,598 A | 4/1986 | Bilstad et al. |
| 4,637,813 A | 1/1987 | DeVries |
| 4,657,529 A | 4/1987 | Prince et al. |
| 4,708,712 A | 11/1987 | Mulzet |
| 4,767,397 A | 8/1988 | Hohenberg et al. |
| 4,781,687 A | 11/1988 | Wall |
| 4,834,890 A | 5/1989 | Brown et al. |
| 4,842,576 A | 6/1989 | Lysaght et al. |
| 4,850,952 A | 7/1989 | Figdor et al. |
| 4,851,126 A | 7/1989 | Schoendorfer |
| 4,887,411 A | 12/1989 | Rondeau et al. |
| 4,898,675 A | 2/1990 | Lavender |
| 4,911,703 A | 3/1990 | Lysaght et al. |
| 4,919,646 A | 4/1990 | Perdriat |
| 4,934,995 A | 6/1990 | Cullis |
| 4,939,081 A | 7/1990 | Figdor et al. |
| 4,968,295 A | 11/1990 | Neumann |
| 4,994,188 A | 2/1991 | Prince |
| 5,015,226 A | 5/1991 | Polaschegg |
| 5,024,231 A | 6/1991 | Feldschuh et al. |
| 5,078,671 A | 1/1992 | Dennehey et al. |
| 5,120,303 A | 6/1992 | Hombrouckx |
| 5,121,470 A | 6/1992 | Trautman |
| 5,171,456 A | 12/1992 | Hwang et al. |
| 5,178,603 A | 1/1993 | Prince |
| 5,200,090 A | 4/1993 | Ford et al. |
| 5,217,426 A | 6/1993 | Bacehowski et al. |
| 5,232,437 A | 8/1993 | Lysaght et al. |
| 5,267,956 A | 12/1993 | Beuchat |
| 5,273,517 A | 12/1993 | Barone et al. |
| 5,298,171 A | 3/1994 | Biesel |
| 5,316,667 A | 5/1994 | Brown et al. |
| 5,321,800 A | 6/1994 | Lesser |
| 5,324,422 A | 6/1994 | Colleran et al. |
| 5,346,472 A | 9/1994 | Keshaviah et al. |
| 5,360,542 A | 11/1994 | Williamson, IV et al. |
| 5,362,291 A | 11/1994 | Williamson, IV |
| 5,370,802 A | 12/1994 | Brown |
| 5,427,695 A | 6/1995 | Brown |
| 5,445,506 A | 8/1995 | Afflerbaugh et al. |
| 5,494,578 A | 2/1996 | Brown et al. |
| 5,496,265 A | 3/1996 | Langley et al. |
| 5,529,691 A | 6/1996 | Brown |
| 5,536,237 A | 7/1996 | Prince et al. |
| 5,549,834 A | 8/1996 | Brown |
| 5,556,749 A | 9/1996 | Mitsuhashi et al. |
| 5,573,678 A | 11/1996 | Brown et al. |
| 5,581,687 A | 12/1996 | Lyle et al. |
| 5,628,915 A | 5/1997 | Brown et al. |
| 5,632,893 A | 5/1997 | Brown et al. |
| 5,637,082 A | 6/1997 | Pages et al. |
| 5,639,382 A | 6/1997 | Brown |
| 5,641,414 A | 6/1997 | Brown |
| 5,651,766 A | 7/1997 | Kingsley et al. |
| 5,653,887 A | 8/1997 | Wahl et al. |
| 5,656,163 A | 8/1997 | Brown |
| 5,658,240 A | 8/1997 | Urdahl et al. |
| 5,676,841 A | 10/1997 | Brown |
| 5,681,273 A | 10/1997 | Brown |
| 5,693,232 A | 12/1997 | Brown et al. |
| 5,712,798 A | 1/1998 | Langley et al. |
| 5,715,731 A | 2/1998 | Koch et al. |
| 5,721,676 A | 2/1998 | Bolden et al. |
| 5,728,060 A | 3/1998 | Kingsley et al. |
| 5,730,883 A | 3/1998 | Brown |
| 5,733,253 A | 3/1998 | Headley et al. |
| 5,759,413 A | 6/1998 | Brown |
| 5,769,811 A | 6/1998 | Stacey et al. |
| 5,770,069 A | 6/1998 | Meryman |
| 5,779,660 A | 7/1998 | Kingsley et al. |
| 5,788,621 A | 8/1998 | Eady |
| 5,792,372 A | 8/1998 | Brown et al. |
| 5,793,969 A | 8/1998 | Kamentsky et al. |
| 5,807,492 A | 9/1998 | Brown et al. |
| 5,812,419 A | 9/1998 | Chupp et al. |
| 5,833,866 A | 11/1998 | Brown |
| 5,853,382 A | 12/1998 | Kingsley et al. |
| 5,885,239 A | 3/1999 | Headley et al. |
| 5,915,240 A | 6/1999 | Karpf |
| 5,930,791 A | 7/1999 | Leu |
| 5,941,842 A | 8/1999 | Steele et al. |
| 5,956,023 A | 9/1999 | Lyle et al. |
| 5,964,724 A | 10/1999 | Rivera et al. |
| 5,970,423 A | 10/1999 | Langley et al. |
| 5,993,370 A | 11/1999 | Brown et al. |
| 6,007,509 A | 12/1999 | Kingsley et al. |
| 6,007,725 A | 12/1999 | Brown |
| 6,019,742 A | 2/2000 | Headley et al. |
| 6,027,441 A | 2/2000 | Cantu et al. |
| 6,027,657 A | 2/2000 | Min et al. |
| 6,039,711 A | 3/2000 | Headley et al. |
| 6,046,761 A | 4/2000 | Echerer |
| 6,059,979 A | 5/2000 | Brown |
| 6,060,022 A | 5/2000 | Pang et al. |
| 6,071,421 A | 6/2000 | Brown |
| 6,074,335 A | 6/2000 | Headley et al. |
| 6,080,322 A | 6/2000 | Deniega et al. |
| 6,099,491 A | 8/2000 | Headley et al. |
| 6,102,883 A | 8/2000 | Kingsley et al. |
| 6,113,554 A | 9/2000 | Gilcher et al. |
| 6,168,561 B1 | 1/2001 | Cantu et al. |
| 6,233,525 B1 | 5/2001 | Langley et al. |
| 6,251,284 B1 | 6/2001 | Bischof et al. |
| 6,251,291 B1 | 6/2001 | Lamphere et al. |
| 6,254,784 B1 | 7/2001 | Nayak et al. |
| 6,256,643 B1 | 7/2001 | Cork et al. |
| 6,261,217 B1 | 7/2001 | Unger et al. |
| 6,296,602 B1 | 10/2001 | Headley et al. |
| 6,315,706 B1 | 11/2001 | Unger et al. |
| 6,348,031 B1 | 2/2002 | Unger et al. |
| 6,348,156 B1 | 2/2002 | Vishnoi et al. |
| 6,398,760 B1 | 6/2002 | Danby |
| 6,413,200 B1 | 7/2002 | Jorgensen et al. |
| 6,497,674 B1 | 12/2002 | Steele et al. |
| 6,524,231 B1 | 2/2003 | Westberg et al. |
| 6,581,011 B1 | 6/2003 | Johnson et al. |
| 6,582,349 B1 | 6/2003 | Cantu et al. |
| 6,585,499 B2 | 7/2003 | Nguyen et al. |
| 6,602,179 B1 | 8/2003 | Headley et al. |
| 6,605,223 B2 | 8/2003 | Jorgensen et al. |
| 6,652,475 B1 | 11/2003 | Sahines et al. |
| 6,666,665 B1 | 12/2003 | Nguyen et al. |
| 6,673,314 B1 | 1/2004 | Burbank et al. |

(56) References Cited

U.S. PATENT DOCUMENTS

| | | | |
|---|---|---|---|
| 6,730,054 B2 | 5/2004 | Pierce et al. | |
| 6,733,433 B1 | 5/2004 | Fell | |
| 6,790,195 B2 | 9/2004 | Steele et al. | |
| 6,827,863 B2 | 12/2004 | Dolecek et al. | |
| 6,852,074 B1 | 2/2005 | Jorgensen et al. | |
| 7,033,512 B2 | 4/2006 | Hlavinka et al. | |
| 7,072,769 B2 | 7/2006 | Fletcher-Haynes et al. | |
| 7,108,672 B2 | 9/2006 | Steele et al. | |
| 7,166,217 B2 | 1/2007 | Holmes et al. | |
| 7,241,281 B2 | 7/2007 | Coelho et al. | |
| 7,279,107 B2 | 10/2007 | Hogberg et al. | |
| 7,347,932 B2 | 3/2008 | Holmes et al. | |
| 7,413,665 B2 | 8/2008 | Holmes et al. | |
| 7,430,478 B2 | 9/2008 | Fletcher-Haynes et al. | |
| 7,438,679 B2 | 10/2008 | Hlavinka et al. | |
| 7,442,178 B2 | 10/2008 | Chammas | |
| 7,497,944 B2 | 3/2009 | Hogberg et al. | |
| 7,674,221 B2 | 3/2010 | Hudock et al. | |
| 7,766,809 B2 | 8/2010 | Hudock et al. | |
| 7,916,890 B2 | 3/2011 | Steven et al. | |
| 8,070,665 B2 | 12/2011 | Dolecek et al. | |
| 2002/0054101 A1* | 5/2002 | Beatty | G06Q 10/06 715/764 |
| 2003/0154108 A1* | 8/2003 | Fletcher-Haynes et al. | 705/3 |
| 2003/0211927 A1 | 11/2003 | Cantu et al. | |
| 2004/0085443 A1* | 5/2004 | Kallioniemi et al. | 348/135 |
| 2006/0052949 A1 | 3/2006 | Fletcher-Haynes et al. | |
| 2008/0147240 A1 | 6/2008 | Hudock et al. | |
| 2009/0106674 A1* | 4/2009 | Bray et al. | 715/762 |
| 2009/0217202 A1* | 8/2009 | Foley | A61M 1/3693 715/810 |
| 2010/0049542 A1* | 2/2010 | Benjamin | G06F 19/366 705/2 |

FOREIGN PATENT DOCUMENTS

| | | |
|---|---|---|
| EP | 0014093 B1 | 5/1983 |
| EP | 0096217 A2 | 12/1983 |
| EP | 0165751 A2 | 12/1985 |
| EP | 0214803 A2 | 3/1987 |
| EP | 0350495 B1 | 8/1992 |
| EP | 0536594 A1 | 4/1993 |
| EP | 0580299 A1 | 1/1994 |
| EP | 0284764 B1 | 5/1994 |
| EP | 0235160 B1 | 6/1994 |
| EP | 0587257 B1 | 10/1998 |
| EP | 0578086 B1 | 8/2001 |
| EP | 1208856 A2 | 5/2002 |
| FR | 2390173 A1 | 12/1978 |
| GB | 2176717 A | 1/1987 |
| NL | 1008210 | 8/1999 |
| WO | 84/00112 A1 | 1/1984 |
| WO | 88/01880 A1 | 3/1988 |
| WO | 88/05691 A1 | 8/1988 |
| WO | 92/00145 A1 | 1/1992 |
| WO | 93/12888 A1 | 7/1993 |
| WO | 94/11093 A1 | 5/1994 |
| WO | 95/03107 A1 | 2/1995 |
| WO | 00/54823 A1 | 9/2000 |
| WO | 00/54824 A1 | 9/2000 |
| WO | 00/78374 A1 | 12/2000 |
| WO | 01/02979 A2 | 1/2001 |
| WO | 03/026802 A2 | 4/2003 |
| WO | 03/089027 A2 | 10/2003 |
| WO | 2006/054828 A1 | 5/2006 |

OTHER PUBLICATIONS

Baxter Healthcare Corporation, Fenwal Division, "CS-3000 Plus Blood Cell Separator Operator's Manual", 1987, Baxter Healthcare Corporaion.

COBE Laboratories, Inc., "COBE Sprectra Apheresis System, Operator's Manual, Section 1", 1991, Cobe BCT, Inc., Lakewood, Colorado.

European Search Report, European Application No. 06076187.1, Oct. 19, 2006.

Fresenius, "Fresenius MT AS 104 Blood Cell Separator, Operating Instructions, Sections 2-4, 6 portions of 7", undated.

Haemonetics Corporation, "Haemonetics Mobile Collection System Owner's Operating and Maintenance Manual", 1991, Haemonetics Corporation.

International Search Report and Written Opinion, PCT/US06/21674, Oct. 20, 2006.

* cited by examiner

Protocol 1

| Operator ID | Whole Blood | Platelet | Plasma | RBC | Leukocytes |
|---|---|---|---|---|---|
| Badge | Red 1 | Yellow 1 | Yellow 2 | Red 2 | Brown |

*FIG. 7A*

Protocol 2

| Operator ID | Whole Blood | Platelet | Plasma | RBC |
|---|---|---|---|---|
| Badge | Red 1 | Yellow 1 | Yellow 2 | Red 2 |

*FIG. 7B*

GENERATING PROCEDURES FOR ENTERING DATA PRIOR TO SEPARATING A LIQUID INTO COMPONENTS

CROSS-REFERENCE TO RELATED APPLICATIONS

This application claims priority to U.S. Provisional Patent Application No. 61/664,566, filed Jun. 26, 2012, and entitled PROCEDURES FOR ENTERING DATA, which is hereby incorporated by reference in its entirety as if set forth herein in full.

BACKGROUND

It is common to process a variety of liquids into liquid components that are then utilized separately, once separated. In some instances, being able to trace the origin of a component of a liquid can be important. For example, when processing whole blood into blood components, it is important to be able to keep track of the origin of the blood components, e.g., to trace the origin to the original donor of the whole blood. If there is a pathogen detected in a blood component, the ability to track down the original donor, as well as make sure that none of the blood components are given to other patients, can potentially prevent the spread of pathogens in a population.

To implement tracking of liquid components, there is commonly a procedure for entering data prior to separating the liquids. In the example of blood components, an operator of a blood separator will typically scan a number of barcodes located on a container holding whole blood as well as on containers in which the blood components will be stored after being separated from the whole blood.

A procedure generated by an administrator indicates which barcodes should be scanned and the sequence in which the barcodes should be scanned. The tools available to an administrator for generating the procedure are limited. The procedures may be generated using text within a table or matrix. When creating the procedures, it can be difficult for an administrator to look at a table and determine what barcodes have already been selected for scanning as part of the procedure, and which have not yet been included in the procedure. Also, use of a table makes it difficult for an administrator to create a procedure that is efficient from the perspective of an operator. For example, an administrator may not appreciate that a procedure requires an operator to scan a barcode on a first container, followed by a barcode on a third container, and then scan a second barcode on the first container. As a result, the procedure may be complicated, inefficient, and lead to errors in entering the correct data, i.e., scanning the correct barcodes.

It is in light of these and other considerations that the embodiments described below have been invented. The embodiments described below are not limited to solving any particular problem, including the specific problems mentioned above. Therefore, this background section should not be used to limit any embodiment of the present invention, including the claimed embodiments.

SUMMARY

Described are embodiments that are useful for generating procedures for entering data prior to separating liquid into liquid components. The embodiments allow an administrator to understand the workflow of an operator that will be following the procedures. This allows the administrator to generate procedures that are efficient and less prone to errors by the operator performing the procedures. The embodiments are applicable to any procedure for entering data prior to a process. In one particular embodiment, the present invention is useful in generating procedures for entering data prior to separating whole blood into blood components.

Other features and advantages of the invention will appear from the following description and accompanying drawings, which are to be considered exemplary only, and are not intended to be limiting.

BRIEF DESCRIPTION OF THE DRAWINGS

Non-limiting and non-exhaustive embodiments are described with reference to the following figures.

FIGS. 7A-7B illustrate graphical elements according to another embodiment of the present invention.

DETAILED DESCRIPTION

The principles of the present invention may be further understood by reference to the following detailed description and the embodiments depicted in the accompanying drawings. It should be understood that although specific features are shown and described below with respect to detailed embodiments, the present invention is not limited to the embodiments described below.

Described are embodiments that are useful for generating procedures for entering data prior to separating liquid into liquid components. The embodiments allow an administrator to appreciate the workflow of an operator that will be following the procedure. This allows the administrator to generate procedures that are efficient and less prone to errors by the operator performing the procedures. The embodiments are applicable to any procedures for entering data prior to a process. In one particular embodiment, the present invention is useful in generating procedures for entering data prior to separating whole blood into blood components. Although particular features are described below, this description is provided merely for illustrative purposes and the embodiments of the present invention may include features not described below. Also some embodiments may include a portion of the features described below but not include other features. These variations are all within the scope of the present invention.

Figure 1:
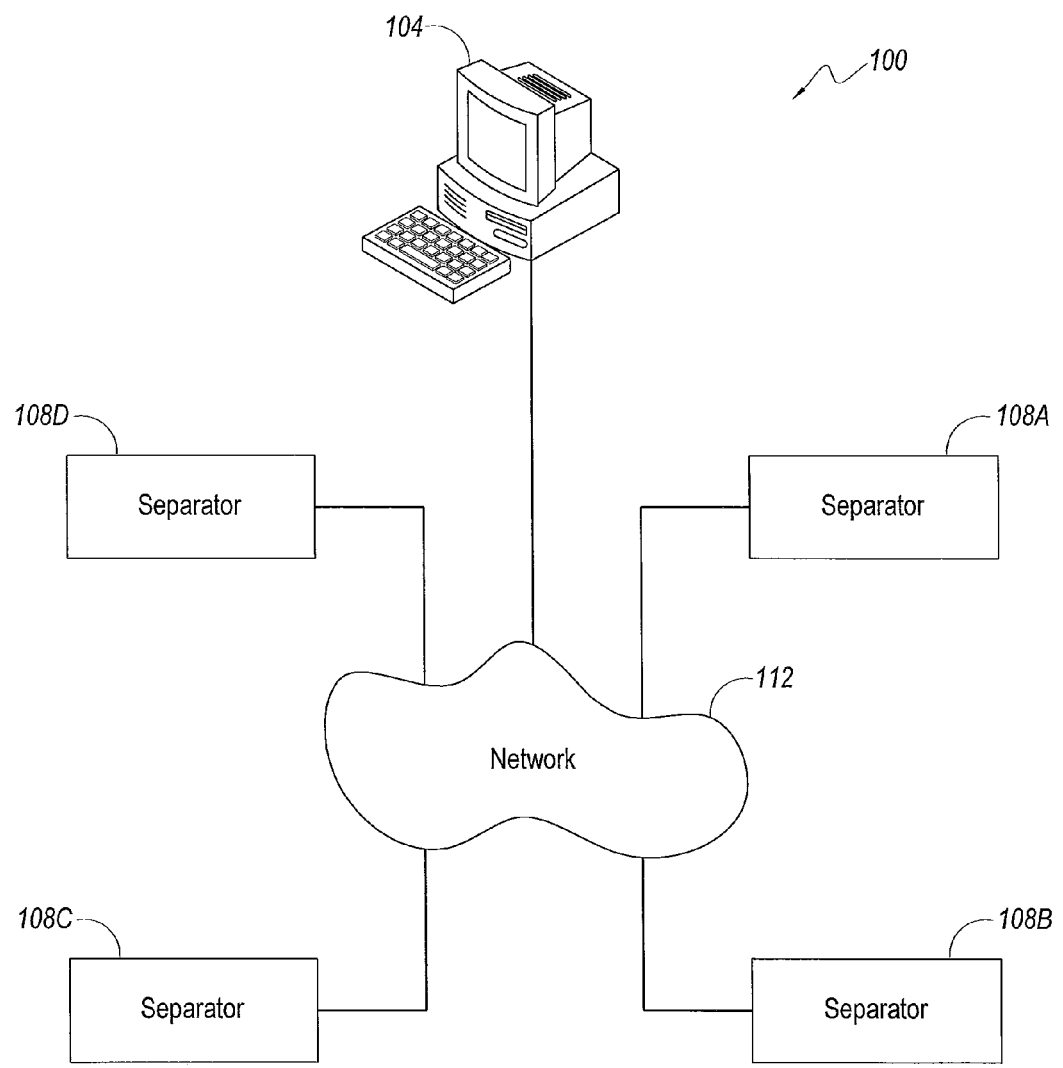
FIG. 1 illustrates a system for separating liquid into liquid components that may be used to implement embodiments of the present invention.

FIG. 1 illustrates a system 100 for separating liquid into liquid components that may be used to implement embodiments of the present invention. System 100 includes a first computing device 104 and separators 108A-D, which also include computing devices. In one embodiment, separators 108A-D are whole blood separators that separate blood into blood components such as plasma, platelets, white blood cells, and red blood cells. Examples of automated whole blood separators that may be used as separators 108A-D include the ATREUS® and OrbiSac whole blood processing systems manufactured by Terumo BCT of Lakewood, Colo.

Computing device 104 is connected to separators 108A-D through network 112. Network 112 is in embodiments merely a direct wired or wireless connection between device 104 and one or more of the separators 108A-D. In other embodiments, network 112 utilizes one or more local area networks (LANs), one or more wide area networks (WANs), or a combination of LAN(s) and WAN(s).

In embodiments, computing device 104 provides management functionality that is used in configuring separators 108A-D. For example, computing device 104 may store protocols that separators 108A-D follow in processing liquids. In one embodiment, the protocols include a series of device commands that separators 108A-D follow to ensure proper separation of a liquid, e.g., blood, and also includes the number of liquid components generated during the separation. The protocols may be stored at computing device 104 and transmitted through network 112 to separators 108A-D.

Computing device 104 may also store and manage data entered into separators 108A-D by an operator. In accordance with embodiments of the present invention, computing device 104 is used to create procedures that operators of separators 108A-D follow before processing liquid in the separators 108A-D. The procedures are generated by an administrator utilizing computing device 104, and once generated are transmitted to separators 108A-D. Separators 108A-D execute the procedures and prompt the operator to enter data according to the procedures. In some embodiments, when data is entered during the procedure, it is validated by computing device 104 before allowing a next step in the procedure. For example, if the procedure requires a particular type of data, e.g., operator identifier, to be entered, data entered by an operator may be validated to ensure that it is of the required type. In these embodiments, separators 108A-D periodically transmit requests to validate received data to computing device 104, which replies to the requests with validation responses indicating whether the data has been validated.

Figure 2:
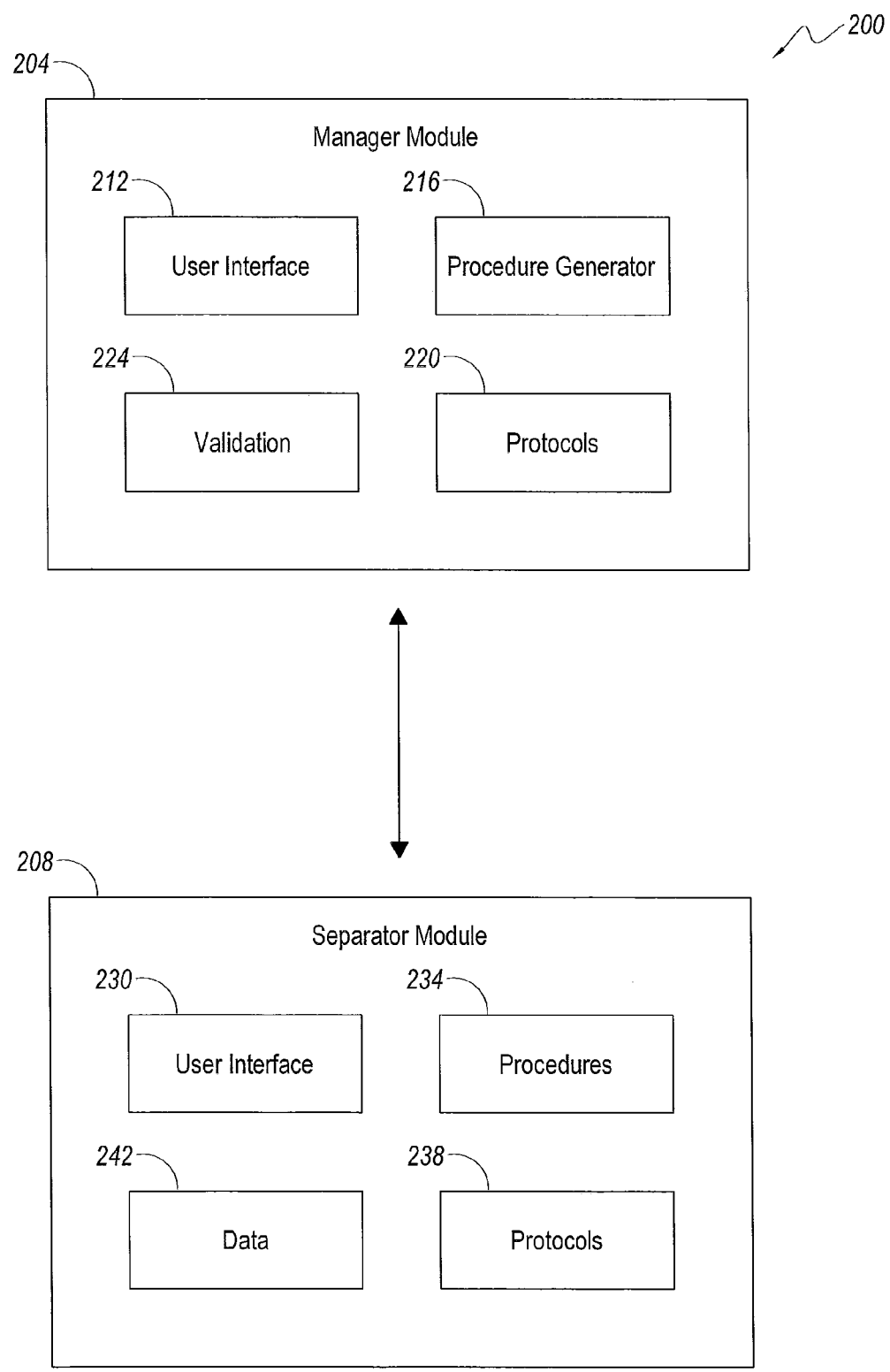
FIG. 2 illustrates a block diagram showing a software environment in which some embodiments of the present invention are implemented.

FIG. 2 illustrates a block diagram of a software environment 200 in which some embodiments of the present invention are implemented. In embodiments, manager module 204 is executed by device 104 (FIG. 1) and separator module 208 is executed by separators 108 A-D (FIG. 1). It is noted, however, that in some embodiments, manager module 204 may be executed on the same device as separator module 208. The term "module" is used herein to generally refer to code, instructions, routines, programs, objects, components, data structures and the like that are executed and interact to perform tasks. Software environment 200 may, in some embodiments, be implemented in a distributed computing environment where tasks are performed on different devices that are linked through a communications network. In a distributed computing environment, modules, or portions of modules, may be located on different devices.

As shown in FIG. 2, separator module 208 includes a user interface 230, procedures 234, protocols 238, and data 242. The user interface 230 allows an operator to select a protocol from protocols 238 for separating liquid into liquid components. User interface 230 can then be used during procedures, e.g., pre-processing procedures prior to separating liquid into liquid components. Data module 242 is used to store data that is entered during the procedures 238. Also data module 242 may also communicate with portions of manager module 204, such as validation module 224, to validate data entered during the procedures 234.

Manager module 204 includes a user interface module 212, a procedure generator module 216, protocols 220, and a validation module 224. As can be appreciated, an administrator utilizes user interface module 212 to interact with manager module 204. For example, an administrator may store protocols 220 and transmit protocols 220 to separator module 208 using user interface 212. Also, an administrator may configure validation module 224 using user interface 212. It is noted that although user interface 212 is described as a single module that allows a user to interact with other modules, in other embodiments, each module, such as validation module 224 and procedure generator 216 may have a separate user interface module.

Through user interface module 212, an administrator can also interact with procedure generator 216. In accordance with some embodiments, user interface 212 provides graphical elements that allow an administrator to easily create procedures for entering data prior to processing a liquid into liquid components. As described in greater detail below, user interface 212 provides graphical elements that reflect the workflow of someone who would implement the procedure being created. In this way, the administrator can appreciate how an operator would implement the procedure and identify and correct any inefficiencies or other potential problems in the procedure. An administrator can therefore generate procedures that are efficient, simple, and less likely to result in an error by the operator.

Figure 3:
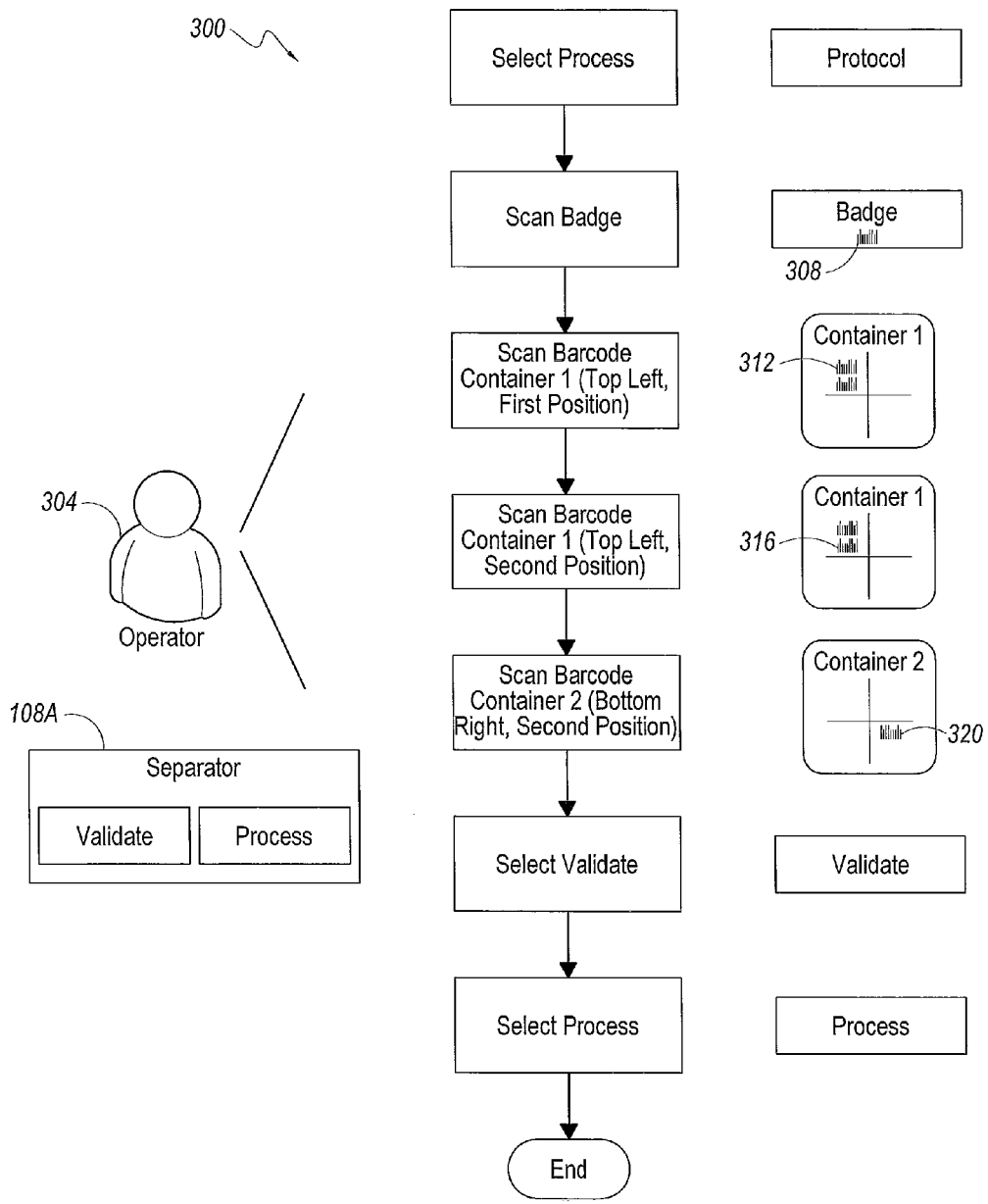
FIG. 3 illustrates an example of a workflow that an operator may perform when separating a liquid into components.

FIG. 3 illustrates an example of a workflow 300 that an operator 304 may follow when performing a pre-processing procedure to enter data prior to separating a liquid into components. In this example, an operator 304 is separating whole blood into blood components using separator 108A (FIG. 1A), which in this example is a whole blood separator. Workflow 300 is an example of the actual steps that operator 304 may perform as part of the pre-processing procedure.

Workflow 300 begins by operator 304 selecting a process for separating the whole blood into blood components, which may involve the operator using a user interface of separator 108A to select a particular protocol. As part of a pre-processing procedure, the operator may be required to enter an operator identifier. In this example, a data identifier, e.g., barcode 308, on the operator's badge is scanned by the operator. The procedure may next call for a donor (person who donated the blood) identifier to be entered. Operator 304 then scans a second data identifier, e.g., barcode 312, in a first position in the top left corner of a label on the container (a blood bag) storing the whole blood.

The workflow 300 may next call for a collection facility identifier to be entered. Operator 304 then scans a third data identifier, e.g., barcode 316, in a second position in the top left corner of the label on the container storing the whole blood. The procedure may next call for a component identifier to be entered. Operator 304 then scans a fourth data identifier, e.g., barcode 320, in a first position in the bottom right corner of a label on a second container that will hold a blood component. The procedure may then require validation of the entered data, which the operator does by selecting a validation option (e.g., through a displayed user interface or a physical button) as the operator's next step in the workflow 300. Finally, the operator can select to process, i.e., separate, the blood by selecting a process option (e.g., through a displayed user interface or a physical button).

As workflow 300 illustrates, an operator that performs a pre-processing procedure must physically perform a number of steps to enter data before blood is separated. As can be appreciated, if the procedure requires the operator to enter data in an inefficient manner, the operator may not enter the data properly. For example, if the procedure requires an operator's workflow to scan barcode 312 first, followed by barcode 320, and then barcode 308, an operator may get confused having to go from one container to another and then to a badge. As noted above, having a table that lists the steps and locations for scanning of data identifiers (as is currently done), makes it difficult for an administrator to appreciate the actual workflow of an operator when performing a procedure.

Figure 4:
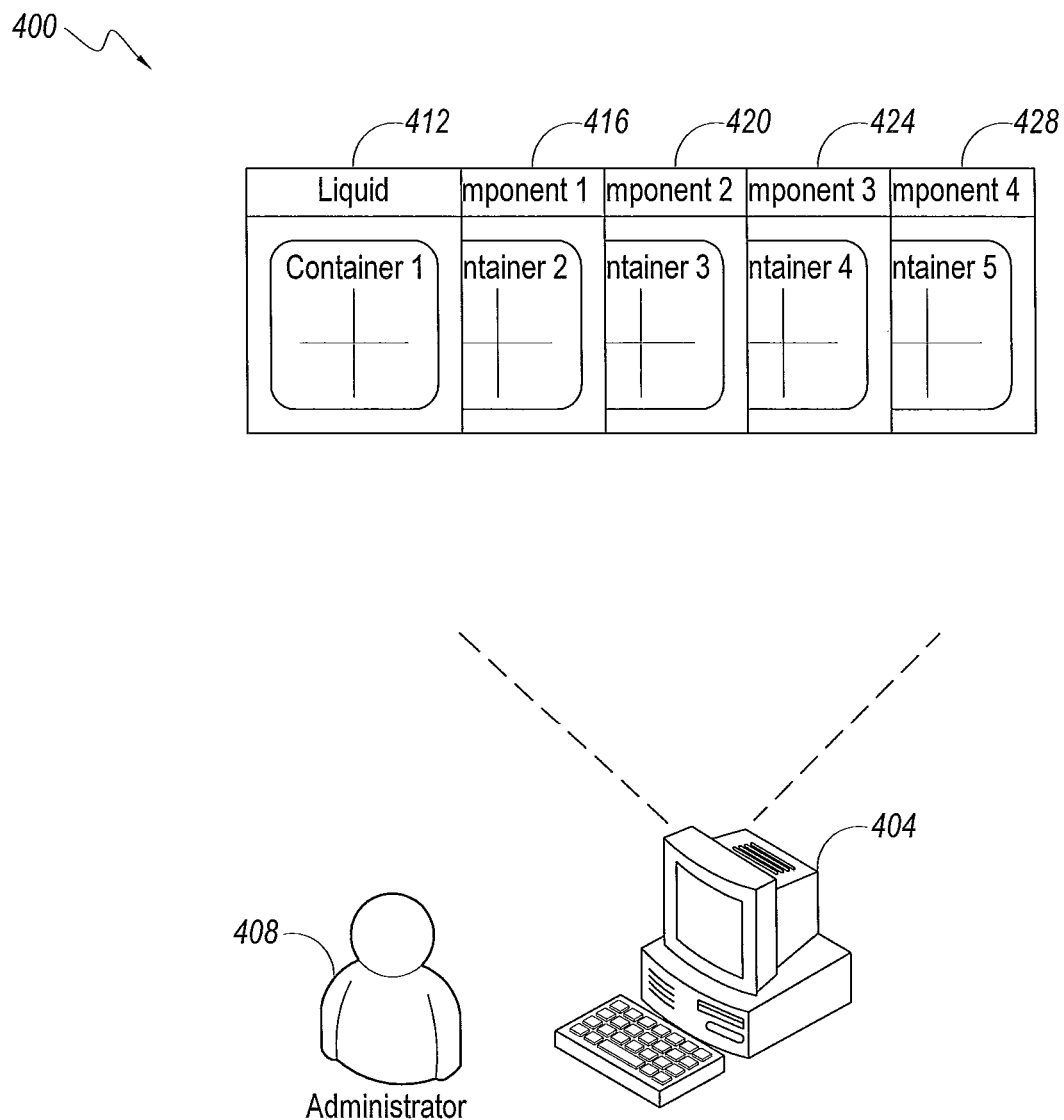
FIG. 4 illustrates an embodiment of a user interface with graphical elements according to one embodiment of the present invention.

FIG. 4 illustrates an embodiment of a user interface 400 with a number of graphical elements (412, 416, 420, 424, and 428), according to one embodiment of the present invention. User interface 400 is an example of one embodiment of user interface 212 described above with respect to FIG. 2. In FIG. 4, elements (412, 416, 420, 424, and 428) are graphical elements that may correspond to containers that are used to hold the liquid or liquid components. In addition, each of the graphical elements (412, 416, 420, 424, and 428) includes a name of a liquid component or of the liquid, which also assists the administrator in creating pre-processing procedures. Although shown as windows, in other embodiments graphical elements (412, 416, 420, 424, and 428) may be icons, pop-up boxes, dialog boxes, balloons, images, combinations thereof, or other visual elements. User interface 400 also includes additional features not shown in FIG. 4 in order to avoid obscuring features of the graphical elements (412, 416, 420, 424, and 428).

Administrator 408 utilizes user interface 400 displayed on device 404, namely the graphical elements (412, 416, 420, 424, and 428), to create a procedure for entering data prior to processing of the liquid into components. In operation, administrator 408 selects one of the graphical elements (412, 416, 420, 424, and 428) to begin creating the procedure.

Figure 5A:
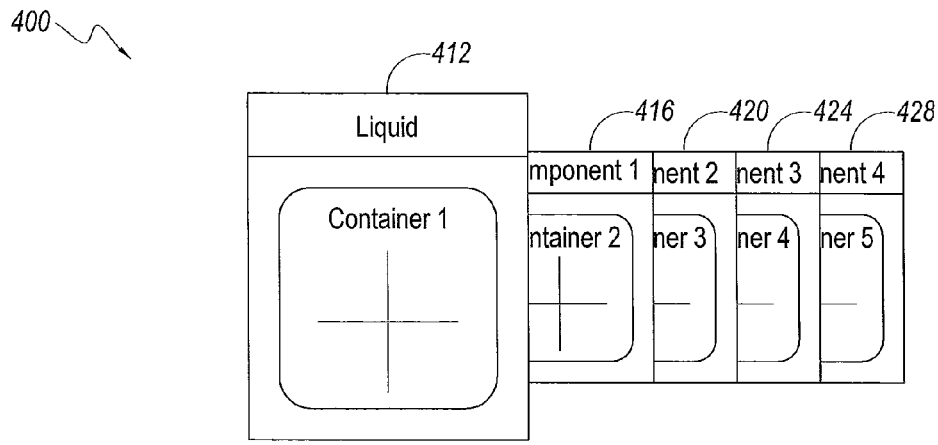
FIG. 5A-5C illustrates highlighting of graphical elements positioned in a carousel according to an embodiment of the present invention.
Figure 5B:
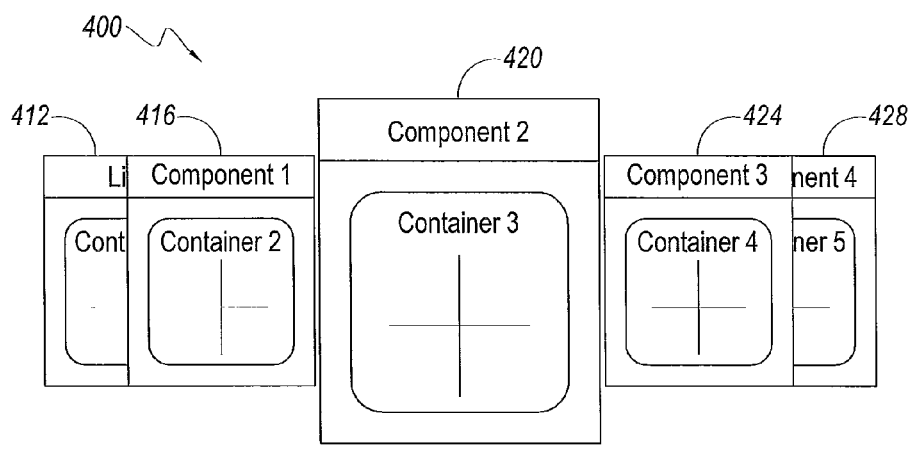
Figure 5C:
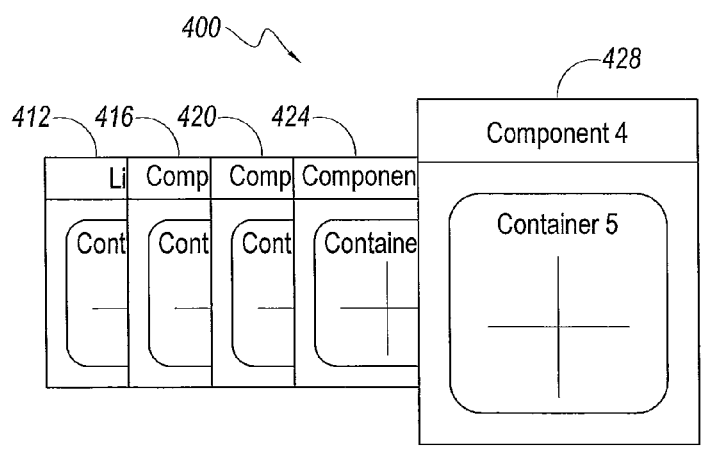

In FIGS. 5A-5C, the graphical elements (412, 416, 420, 424, and 428) are displayed as a carousel, in a predetermined order, which in some embodiments can be changed by administrator 408. As shown in FIGS. 5A-5C, when one of the graphical elements (412, 416, 420, 424, and 428) is selected, it is highlighted. In FIG. 5A, graphical element 412 is selected by administrator 408, e.g., using a touch screen, a mouse, keyboard, voice recognition, or other input device. In response to the selection, graphical element 412 is highlighted by being displayed in the center of user interface 400 and is made larger than the other graphical elements (416, 420, 424, and 428). All of the graphical elements (412, 416, 420, 424, and 428) remain in the original order in the carousel.

In FIG. 5B, graphical element 420 has been selected by administrator 408. In response to the selection, graphical element 420 is displayed in the center of user interface 400 and is made larger than the other graphical elements (412, 416, 424, and 428). All of the graphical elements (412, 416, 420, 424, and 428) remain in the original order in the carousel, with graphical elements 412 and 416 displayed on the left of graphical element 420, and graphical elements 424 and 428 displayed on the right of graphical element 420.

FIG. 5C illustrates the situation when graphical element 428 has been selected and is displayed in the center of user interface 400 and is made larger than the other graphical elements (412, 416, 420, and 424), which remain in order on the left side of graphical element 428.

As can be appreciated, the ability to visually see the graphical elements, which are associated with containers used in the actual process, helps the administrator 408 to visualize the workflow of an operator who will implement the procedure being created. It is noted that although in the embodiments shown in FIGS. 5A-5C, the highlighting involves increasing the size and changing the position of the selected element. In other embodiments, the highlighting may be effected in any suitable way that distinguishes the selected graphical element from the unselected graphical elements, including differences in size, style, font, color, lighting, or other visual feature.

Figure 6A:
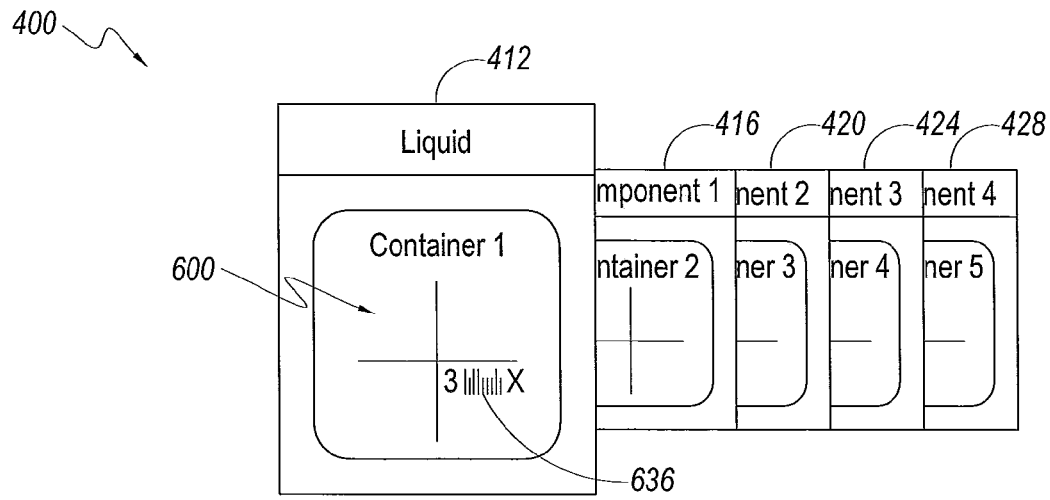
FIGS. 6A-6B illustrate a window for creating a procedure that includes scanning data identifiers according to an embodiment of the present invention.
Figure 6B:
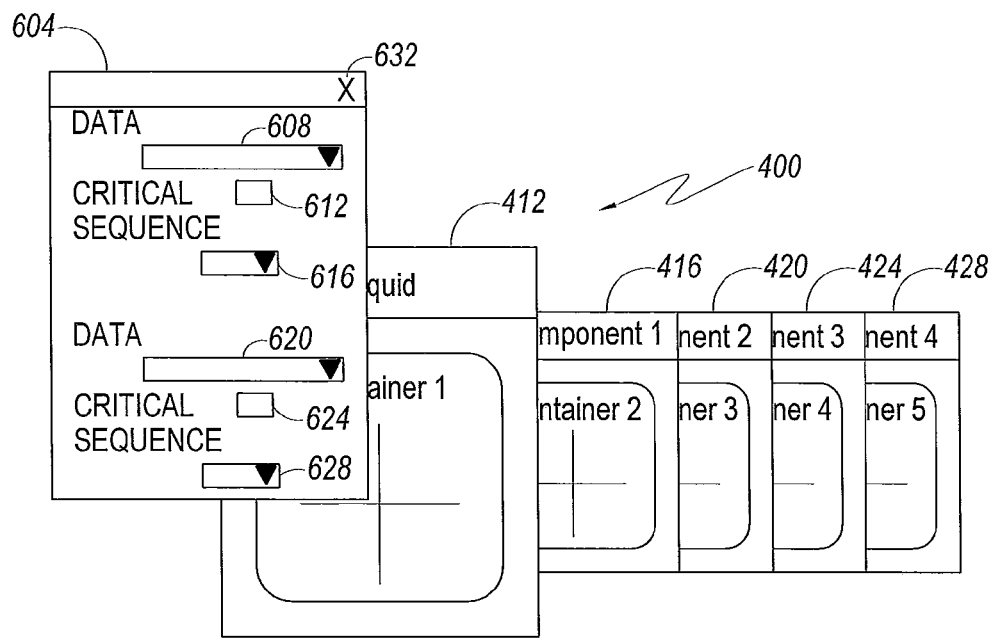

Once administrator 408 selects a graphical element, the administrator 408 can further define the procedure. In this embodiment, the procedure includes entering data from a label on each container. Each label includes four regions and data identifiers (e.g., barcodes, text, radio frequency identifiers, magnetic strips, or combinations thereof) within the four regions. Accordingly, as shown in FIGS. 6A and 6B, the graphical elements (412, 416, 420, 424, and 428) include four regions that correspond to regions in the labels that will be on the containers. In one embodiment, two data identifiers may be positioned within each of the four regions.

FIG. 6A illustrates user interface 400 after administrator 408 has selected graphical element 412. Administrator 408 provides input into one of the regions, region 600. In response to the input, window 604 is displayed, as shown in FIG. 6B. Window 604 allows administrator 408 to indicate a data type for a first data identifier that will be located in a region of the label on the container holding the liquid that corresponds to region 600 in the graphical element 412. The data type may be selected from drop down menu 608. In the embodiments in which whole blood is separated into blood components, the data type may be for example, a donor identifier, a facility identifier, a component identifier, or other types of data.

In addition, window 604 also allows administrator 408 to indicate whether the data to be entered from the data identifier is critical. Administrator 408 may decide that there is some information that is critical to the procedure. If the proper data is not received, then the operator should not be allowed to continue the procedure or processing of the liquid. Box 612 can be checked by administrator 408 to indicate that this data is critical. Information regarding whether the data is critical, e.g., whether box 612 is checked or not, may be referred to herein as critical information.

Window 604 also allows administrator 408 to provide a sequence number, which indicates the order in which the data should be entered, e.g., the order in which an operator should scan the data identifiers. Drop down menu 616 is used to select the sequence number. Administrator 408 therefore has the flexibility to determine what data should be entered by the operator first, second, and so on.

As indicated above, in this embodiment each region may include two data identifiers. As a result, the window 604 includes drop down menu 620, which can be used to select the data type for a second identifier. Box 624 can be used to indicate whether the second identifier is critical. Finally, drop down menu 628 can be used to indicate a sequence number for the second data identifier.

In the embodiment shown in FIGS. 6A-6B, window 604, or a similar window, is displayed when administrator 408 clicks on any of the four regions on the graphical elements (412, 416, 420, 424, and 428). Administrator 408 can, as described above, indicate data type, critical information, and sequence number using window 604 for each region.

As can be appreciated, graphical elements (412, 416, 420, 424, and 428) and window 604 allow administrator 408 to easily visualize a workflow that an operator who follows the pre-processing procedure will perform. In other words, administrator 408 can visualize what data identifier, on which container, and in what order will an operator have to scan data identifier. Administrator 408 can therefore easily see when procedures are inefficient, such as requiring an operator to scan a data identifier from one container followed by having to move to a second container before all of the data identifiers from the first container are scanned. Using the embodiments shown in FIGS. 4-6B an administrator 408 can easily adjust the procedure by changing sequence numbers using window 604 to ensure that all the scans from a container are made before moving on to a second container.

After data identifier positions, data types, critical information, and sequence information have been received from an administrator, window 604 can be removed from being displayed, such as by clicking on a close button 632. However, indicators of the selections made by the administrator remain displayed on a graphical element. For example, in region 636, an administrator has previously positioned an identifier (a barcode). As is illustrated, a sequence number "3" is shown next to the identifier indicating that an administrator has assigned this as the third data identifier to be scanned in the process. Furthermore, an indicator "X" indicates that the administrator has decided that the data is critical. The indications that are displayed on the graphical element allow an administrator to easily see the position of the data identifiers as well as their sequence in the procedure. This information is helpful in creating the procedure and visualizing a workflow of the operator. As can be appreciated, the indications displayed on the graphical elements are not limited to those shown in region 636. For example, the indication of the critical nature of the data identifier may be indicated by some other feature such as a check mark, icon, other text, or highlighting of the data identifier.

Some embodiments provide for additional security features. For example, an administrator may need additional privileges to change an existing procedure. In these embodiments, an administrator may be prompted for additional credentials before window 604 is displayed. In other embodiments, window 604 may be displayed, however an administrator may have to input additional credentials before being able to make changes. This is merely one example, and other embodiments of the present invention may include different security features that limit what an administrator can do without providing additional credentials.

FIGS. 7A and 7B illustrate user interface 400 displaying graphical elements (700, 704, 708, 712, 716, and 720) according to another embodiment of the present invention. The graphical elements (700, 704, 708, 712, 716, and 720) are used in some embodiments in which the liquid being processed is blood. The graphical elements (700, 704, 708, 712, 716, and 720) include an element for whole blood (704) and a graphical element for each blood component to be separated from whole blood (708, 712, 716, and 720). The graphical elements also include a graphical element 700 for an operator identifier. In procedures for separating blood into blood components, it is common to begin with a step of entering information that identifies an operator. User interface 400 can therefore be preconfigured to display graphical element 700 when the pre-processing procedure being created is for a whole blood separation process.

FIGS. 7A and 7B illustrate additional features of some embodiments of the present invention. Graphical elements 704, 708, 712, 716, and 720 include the name of the liquids that will be stored in the containers that are associated with the graphical elements. Graphical element 704 includes the text "whole blood," graphical element 708 includes the text "platelet," graphical element 712 includes the text "plasma," graphical element 716 includes the text "rbc" which stands for red blood cells, and graphical element 720 includes the text "leukocytes." In addition, each of the graphical elements also include a color, such as shades of red, yellow, orange, brown, black, or white, that reflects the actual color of the whole blood and blood components. It is noted that the colors will be different in those embodiments in which the liquid being processed is of a different color and something other than blood. The entire graphical element may be colored, in some embodiments, or portions of the graphical elements such as the representations of the container (e.g., bag or bottle) may be colored in other embodiments. Having the name of the of the blood components (and the whole blood), as well as colors that reflect the actual colors of the components and (whole blood) provides additional visual characteristic for the administrator to appreciate the workflow of an operator that will be performing the procedure.

In embodiments of the present invention, the graphical elements displayed on user interface 400 can be preconfigured and be different for different processes. For example, in FIG. 7A, six graphical elements (700, 704, 708, 712, 716, and 720) are displayed for a first protocol, namely "Protocol 1." Protocols are used in blood separation processes to identify what components will be separated from the blood, as well as to identify the instructions provided to separator machines in order to generate the separated blood components. As shown in FIG. 7B, for "Protocol 2," only five graphical elements (700, 704, 708, 712, and 716) are displayed. User interface 400 can thus be configured to receive a protocol identifier from an administrator, and in response to receiving a specific protocol identifier display different graphical elements depending upon the received protocol identifier. In other embodiments, a standard set of graphical elements are displayed. In these embodiments, an administrator can delete any graphical elements that do not apply to the pre-processing procedure being created by the administrator.

Figure 8:
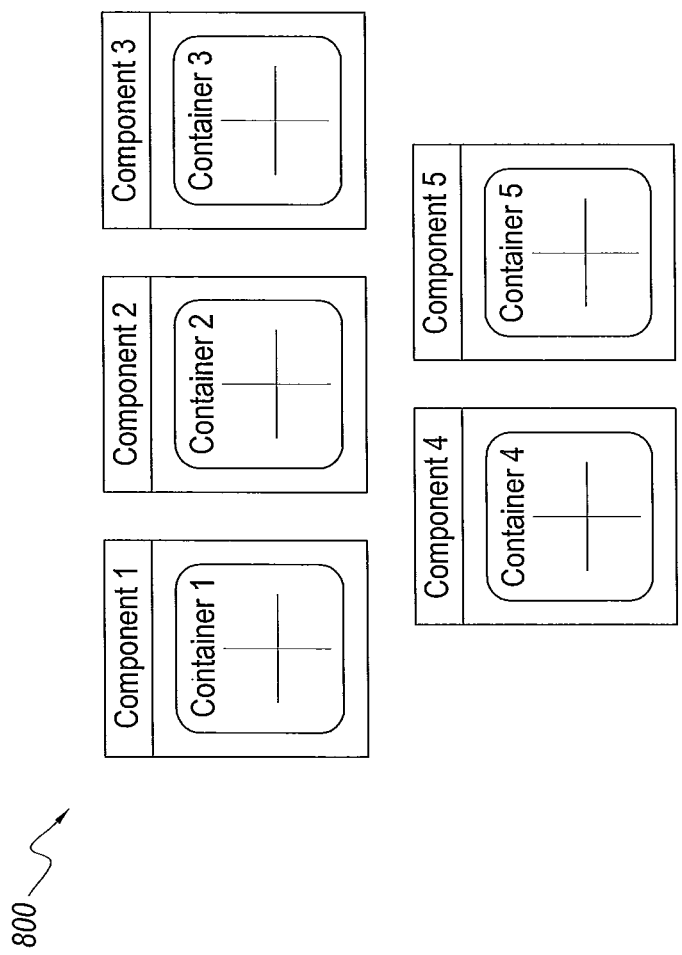
FIG. 8 illustrates graphical elements displayed in order according to a different embodiment of the present invention.

Although the graphical elements in FIGS. 4-7B are displayed in a carousel, the present invention is not limited thereto. FIG. 8 illustrates graphical elements 800 displayed according to another embodiment of the present invention. As can be seen in FIG. 8, the graphical elements 800 are displayed in an order, but not in a carousel. Thus, in some embodiments, graphical elements are not displayed in a carousel but are still displayed in some order that allows an administrator to appreciate the workflow of an operator that will be performing a procedure. FIG. 8 is merely one alternative for displaying graphical elements in an order, according to embodiments of the present invention.

Figure 9:
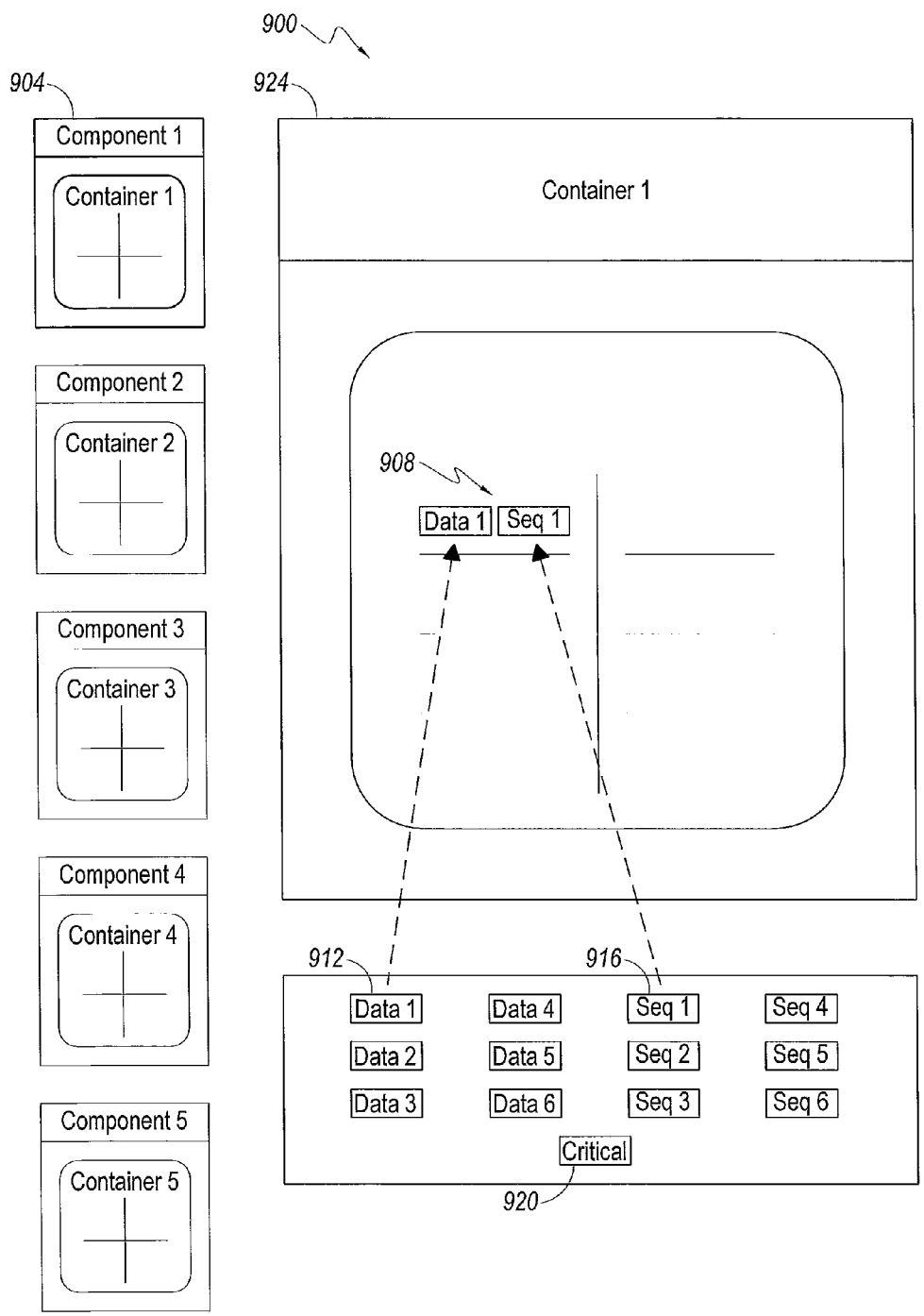
FIG. 9 illustrates graphical elements displayed according to yet another embodiment of the present invention.

FIG. 9 illustrates graphical elements displayed according to yet another embodiment of the present invention. As described above, FIGS. 6A and 6B illustrate one example of how an administrator may assign data types to various regions of graphical elements that correspond to labels on containers. FIGS. 6A and 6B illustrate a window 604 for assigning data types. FIG. 9 illustrates an embodiment of a drag and drop user interface 900 that may be used in other embodiments of the present invention. As can be seen in FIG. 9, user interface 900 includes a number of graphical elements displayed vertically in some order. Graphical element 904 has been selected as indicated by highlighting graphical element 904.

In response, to selecting graphical element 904, a larger copy 924 of graphical element 904 is displayed. An administrator may then interact with portions of the larger copy 924 of the graphical element 904. In particular, an administrator may drag and drop elements onto the larger copy 924. The elements may represent, for example, data types (912), sequence numbers (916), and critical information (920). In FIG. 9, an administrator has dragged a data type 912 and a sequence number 916 into region 908. FIG. 9 provides another embodiment for an administrator to create a procedure that an operator performs to enter data. FIG. 9 also allows an administrator to visualize the work flow that an operator will perform, e.g., when scanning barcodes on containers.

Figure 10:
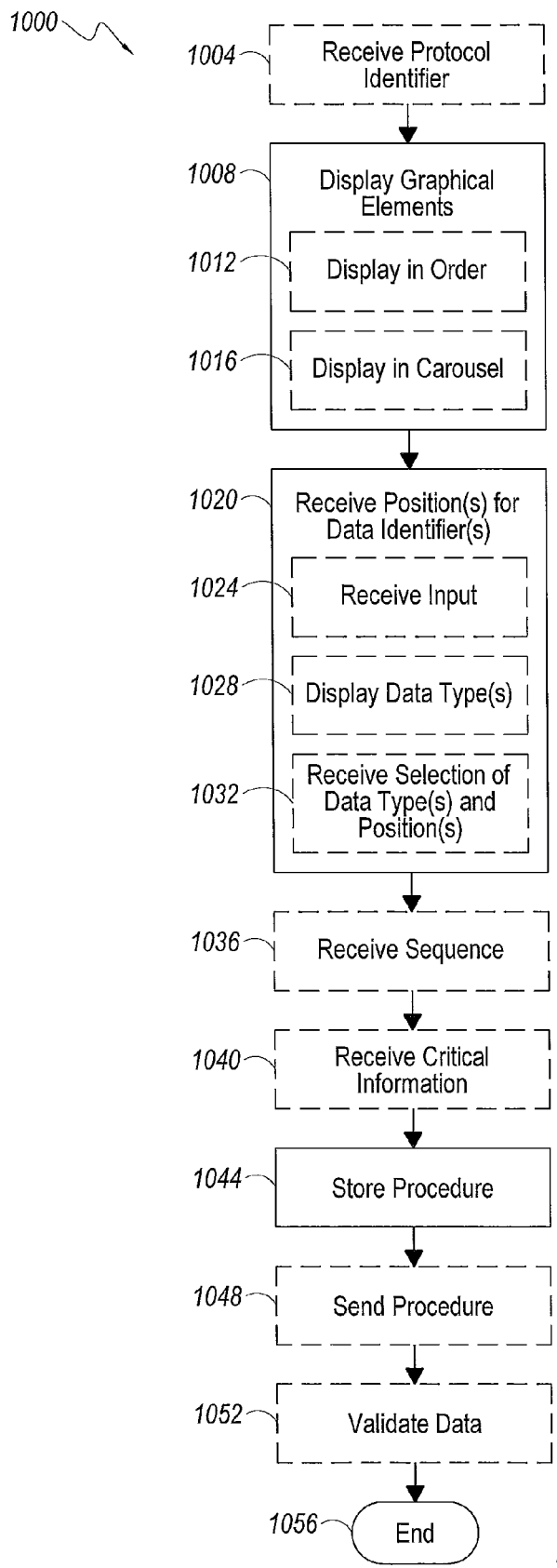
FIG. 10 illustrates a flow 1000 for a process according to an embodiment of the present invention of generating a procedure for inputting data before separating liquid into liquid components.
Figure 11:
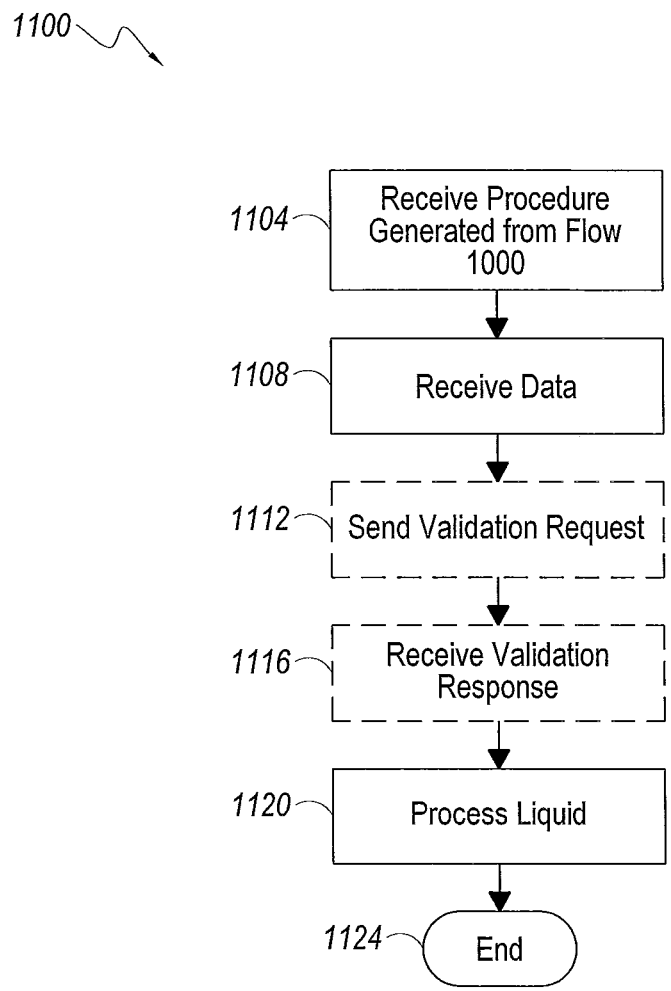
FIG. 11 illustrates a flow 1100 for a process according to an embodiment of the present invention of using a procedure generated by flow 1000 for entering data prior to separating liquid into liquid components.

FIGS. 10 and 11 illustrate flow charts 1000 and 1100 that may be performed in embodiments of the present invention. Although specific components may be described below for performing steps in flow charts 1000 and 1100, the present invention is not limited thereto. For example, some steps may be described as performed by manager module 204 and/or computing device 104, while others are described as performed by separator module 208 and/or separators 108A-D. This is done merely for illustrative purposes, and flow charts 1000 and 1100 are not limited to being performed by any specific components.

FIG. 10 illustrates a flow 1000 for a process, according to an embodiment of the present invention, of generating a procedure for inputting data before separating liquid into liquid components. In some embodiments, the steps of flow 1000 are performed by a software module such as manager module 204 (FIG. 2). Flow 1000 begins at optional step 1004 where a protocol identifier is received. The protocol can identify the components of the liquids that will be separated from the liquid, such as blood components that will be separated from whole blood. The protocol can be entered by an administrator for example before an administrator begins generating a procedure.

Flow 1000 passes from step 1004 to step 1008, where graphical elements are displayed. In one embodiment, the protocol identifier received at step 1004 determines what graphical elements are displayed at step 1008. For example, one protocol identifier may result in six graphical elements being displayed, while a different protocol identifier may result in only five graphical elements being displayed.

Step 1008 may include a number of substeps that are performed as part of step 1008. The graphical elements may for example be displayed in some order at optional substep 1012. Also, the graphical elements may be displayed in a carousel (FIG. 4-7B) at optional substep 1016. These are merely some examples of substeps that may be performed as part of step 1008 and other substeps may be performed in different embodiments. In embodiments, the graphical elements will correspond to containers for a liquid or liquid components that will be processed.

After step 1008, and any associated substeps, flow 1000 passes to step 1020 where positions for data identifiers are received. Step 1020 may also involve a number of substeps. Substep 1024 includes receiving input. The input received at substep 1024 may involve an administrator selecting a region of a graphical element for positioning a data identifier, where the graphical element corresponds to a label on a container. At optional substep 1028, data types may be displayed. The data types may be displayed as a drop down menu (FIG. 6B) or may be displayed as elements that can be dragged (FIG. 9). Substep 1032 involves receiving selection of data types for data identifiers and their positions. This substep in embodiments may involve an administrator dropping a dragged element into a region of a graphical element, or receiving a selection from a drop down menu or entering text. In some embodiments, the substeps of step 1020 may be performed numerous times until all of the data identifiers that will be used during a procedure are positioned.

Step 1020 is followed by optional step 1036 where a sequence is received. At step 1036 an administrator may assign a sequence number to each data identifier positioned at step 1020. The sequence numbers indicate an order in which each data identifier will be entered, e.g., scanned by an operator performing the procedure. Step 1036 may involve entering data into a field, making a selection from a drop down menu, or otherwise making a selection from displayed elements.

Optional step 1040 involves receiving critical information. In this step, an administrator may indicate that certain data to be entered during the procedure is critical and the procedure cannot continue unless the data has been received and/or been received properly. Optional step 1040 may involve entering text into a field, making a selection from a drop down menu, or otherwise making a selection from displayed elements.

At step 1044, the procedure is stored including the positions of the data identifiers, sequence information, and/or any critical information. The procedure may include other information, such as what protocol the procedure should be used with, and whether the procedure includes data validation steps or the procedure includes other reporting steps.

Following step 1044 is optional step 1048 in which the procedure is sent. Step 1044 may involve transmitting the procedure from a management device or module to a separation device or module, e.g., from computing device 104 to separator devices 108A-D (FIG. 1) or from module 204 to module 208 (FIG. 2). The transmitting may be through a network, which may include wired connections, wireless connections, or combinations thereof.

Optional step 1052 involves validating data that may be entered during the procedure. This step may involve determining whether critical data has been entered as indicated by the critical information received at step 1040. In other embodiments, step 1052 may not be related to the critical information but rather involve validating each item of data that is entered as part of the procedure. Flow 1000 ends at 1056.

FIG. 11 illustrates a flow 1100 for a process, according to an embodiment of the present invention, of using a procedure generated by flow 1000 for entering data prior to separating liquid into liquid components, e.g., blood into blood components. In some embodiments, steps of flow 1100 are performed by a separator module such as module 208 (FIG. 2), which may be executing on one or more separator device such as devices 108A-D (FIG. 1).

Flow 1100 begins at step 1104 where a procedure generated according to flow 1000 is received. The procedure may include among other steps, steps for entering data from data identifiers that are on containers. In one embodiment, the data identifiers are barcodes that, in accordance with the procedure, will be scanned by an operator. Following step 1104, data is received at step 1108. This may involve an operator entering data as text or scanning a data identifier such as a barcode, magnetic strip, or radio frequency identifier tag that is on a label placed on a container used to hold liquid during the separation process (e.g., the liquid or liquid components). The data is entered as part of the procedure received at step 1104.

At optional step 1112, a data validation request is sent. The procedure received at step 1104 may require data to be validated. As a result, in some embodiments, a data validation request is sent at step 1112 to validate data. Step 1112 may involve validating each item of data entered or only certain items of data. Following step 1112 is step 1116, which involves receiving a validation response. The response may indicate that the data is validated or may indicate that there is an error and the data has not been validated. This may result in the data needing to be reentered.

It is noted that in some embodiments, the functionality to validate data may be available locally and not require a validation request and response to be sent over a network. In these embodiments, steps 1112 and 1116 may simply involve local requests, commands, or operations.

At step 1120, the liquid is processed. Step 1120 may involve additional steps and procedures not discussed herein. In some embodiments, step 1120 involves using a separator, such as a centrifuge to process liquid into liquid components. Flow 1100 ends at 1124.

Although flows 1000 and 1100 have been described with steps listed in a particular order, the present invention is not limited thereto. In other embodiments, steps may be performed in different order, in parallel, or any different number of times, e.g., before and after another step. Also, as indicated above, flows 1000 and 1100 include some optional steps. However, those steps above that are not indicated as optional should not be considered as essential to the invention, but may be performed in some embodiments of the present invention and not in others.

Figure 12:
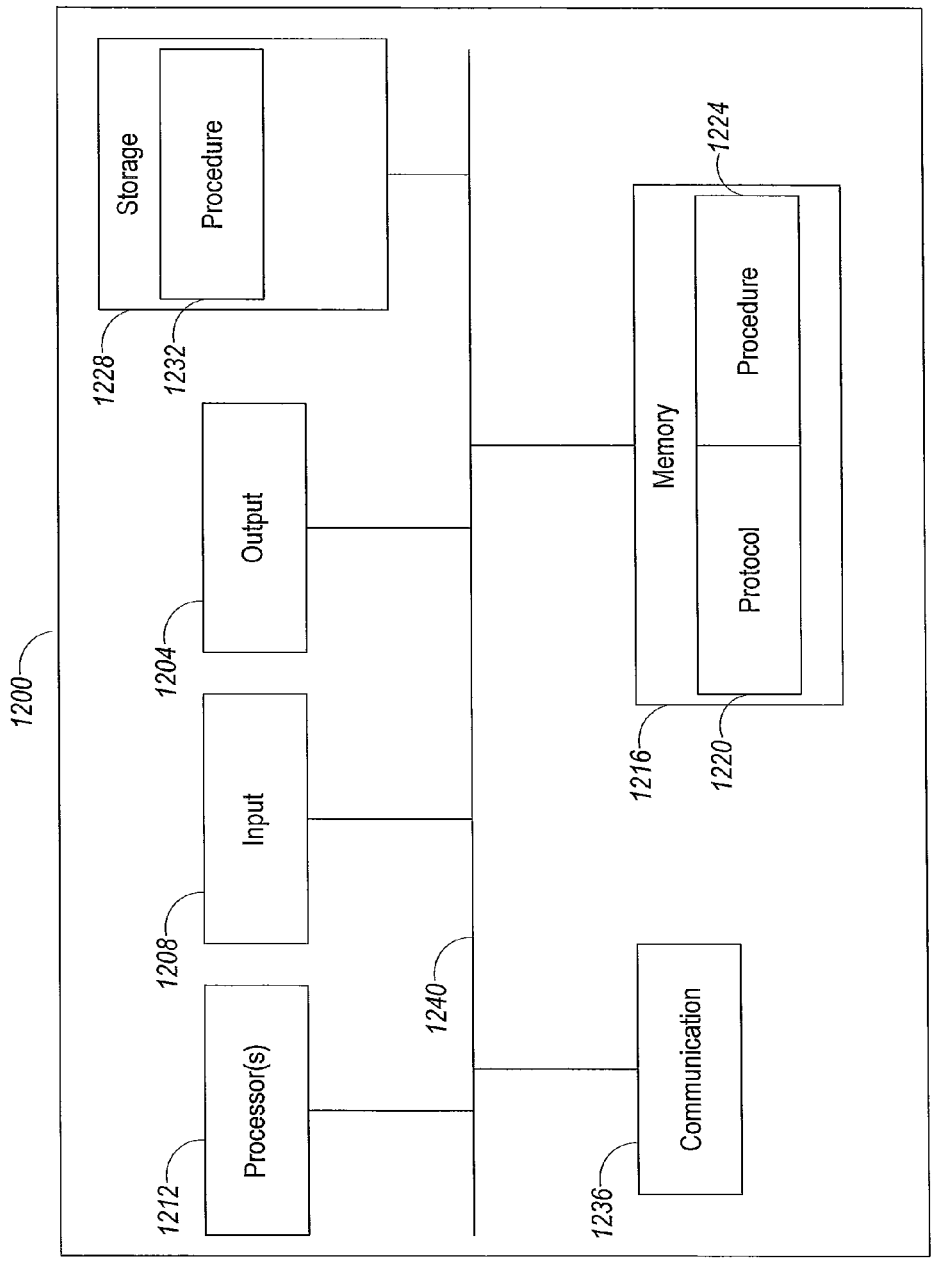
FIG. 12 illustrates a block diagram of a basic computer system that may be used to implement embodiments of the present invention.

FIG. 12 illustrates example components of a basic computer system 1200 upon which embodiments of the present invention may be implemented. For example, computing device 104 as well as separator devices 108A-D may incorporate features of the basic computer system 1200 shown in FIG. 12. Computer system 1200 includes output device(s) 1204, and input device(s) 1208. Output device(s) 1204 include, among other things, one or more displays, including CRT, LCD, and/or plasma displays. Output device(s) 1204 may also include printers, speakers etc. Input device(s) 1208 may include a keyboard, touch input devices, a mouse, voice input device, scanners, etc.

Basic computer system 1200 may also include a processing unit 1212 and memory 1216, according to embodiments of the present invention. The processing unit 1212 may be a general purpose processor operable to execute processor executable instructions stored in memory 1216. Processing unit 1212 may include a single processor or multiple processors, according to embodiments. Further, in embodiments, each processor may be a single core or a multi-core processor, having one or more cores to read and execute separate instructions. The processors may include general purpose processors, application specific integrated circuits (ASICs), field programmable gate arrays (FPGAs), and other integrated circuits.

The memory 1216 may include any tangible storage medium for short-term or long-term storage of data and/or processor executable instructions. The memory 1216 may include, for example, Random Access Memory (RAM), Read-Only Memory (ROM), or Electrically Erasable Programmable Read-Only Memory (EEPROM). Other storage media may include, for example, CD-ROM, tape, digital versatile disks (DVD) or other optical storage, tape, magnetic disk storage, magnetic tape, other magnetic storage devices, etc.

Storage 1228 may be any long-term data storage device or component. Storage 1220 may include one or more of the devices described above with respect to memory 1216. Storage 1228 may be permanent or removable.

Computer system 1200 also includes communication devices 1236. Devices 1236 allow system 1200 to communicate over networks, e.g., wide area networks, local area networks, storage area networks, etc., and may include a number of devices such as modems, hubs, network interface cards, wireless network interface cards, routers, switches, bridges, gateways, wireless access points, etc.

The components of computer system 1200 are shown in FIG. 12 as connected by system bus 1240. It is noted, however, that in other embodiments, the components of system 1200 may be connected using more than a single bus.

In embodiments, separator devices 108A-D (FIG. 1) may include aspects of system 1200. In these embodiments, memory 1216 may store protocols 1220 and procedures 1224, such as procedures generated using flow 1000 (FIG. 10). The separator devices 108A-D can execute the protocols 1220 to separate a liquid, e.g., blood, into components. In other embodiments, computing device 104 (FIG. 1) may include features of system 1200 and may for example utilize storage 1228 to store procedures 1232 created by administrators such as procedures generated using flow 1000 (FIG. 10).

It will be apparent to those skilled in the art that various modifications can be made to the apparatus, systems, and methods described herein. Thus, it should be understood that the embodiments are not limited to the subject matter discussed in the application. Rather, the present disclosure is intended to cover modifications, variations, and/or equivalents. The steps, features, structures, and/or media are disclosed as illustrative embodiments for implementation of the claims and are not intended to limit the claims.

While example embodiments and applications of the present invention have been illustrated and described, it is to be understood that the invention is not limited to the precise configuration and resources described above. Various modifications, changes, and variations apparent to those skilled in the art may be made in the arrangement, operation, and details of the methods and systems of the present invention disclosed herein without departing from the scope of the claimed invention.

What is claimed is:

1. A method of generating a procedure to be used by an operator of a separation device to enter data prior to using the separation device to separate whole blood stored in a container into blood components, the method comprising:

receiving from an administrator an indication of a first blood separation protocol that may be selected by an operator for separating whole blood into components;

in response to receiving the indication of the first blood separation protocol, displaying a first plurality of graphical elements in a carousel, by at least one processor, wherein the first plurality of graphical elements comprise at least: a first graphical element corresponding to a container for holding whole blood, a second graphical element corresponding to a container for holding a first component of the whole blood, a third graphical element corresponding to a container for holding a second component of the whole blood, and a fourth graphical element corresponding to a container for holding a third component of the whole blood, each of the plurality of graphical elements comprising a plurality of displayed regions which are selectable;

receiving, by the at least one processor, a selection of a first region of a plurality of displayed regions in the first graphical element which corresponds to a region of a label on the container holding the whole blood, wherein the region of the label on the container holding the whole blood comprises a first barcode;

in response to receiving the selection of the first region of the plurality of displayed regions in the first graphical element, displaying by the at least one processor a first window for selecting a data type corresponding to the first bar code;

receiving in the first window a selection of a first data type corresponding to the barcode, wherein the first data type is one or more from the group consisting of a donor identifier and a facility identifier;

receiving in the first window a first sequence number associated with the first barcode;

receiving, by the at least one processor a selection of a first region of a plurality of displayed regions in a second graphical element which corresponds to a region of a second label on a container holding a first component of the whole blood, wherein the region of the second label on the container holding a first component of the whole blood comprises a second barcode;

in response to receiving the selection of the first region of the plurality of displayed regions in the second graphical element, displaying by the at least one processor a second window for selecting a second data type corresponding to the second bar code;

receiving in the second window a selection of a second data type corresponding to the second barcode, wherein the second data type is one or more from the group consisting of a donor identifier, a facility identifier, and a component identifier;

receiving, in the second window a second sequence number associated with the second barcode, wherein the second sequence number and the first sequence number determine an order that the operator will scan the first barcode and the second barcode; and storing, in at least one tangible computer readable medium, the first data type, the second data type, the first sequence number, and the second sequence number as part of the procedure.

2. The method of claim 1, wherein the first graphical element comprises text that identifies the container as holding blood.

3. The method of claim 1, further comprising, transmitting the procedure to a separator device.

4. The method of claim 1, further comprising, receiving first data of the first data type during a performing of the procedure.

5. The method of claim 4, wherein the first data is received from a barcode on a first blood bag storing the whole blood.

* * * * *